US008632558B2

(12) United States Patent
Chin et al.

(10) Patent No.: US 8,632,558 B2
(45) Date of Patent: Jan. 21, 2014

(54) SYSTEMS AND METHODS FOR REMOVAL OF INTRAVASCULAR LEADS

(75) Inventors: Albert K. Chin, Palo Alto, CA (US); Lishan Aklog, Scottsdale, AZ (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 0 days.

(21) Appl. No.: 13/010,447

(22) Filed: Jan. 20, 2011

(65) Prior Publication Data

US 2011/0213398 A1    Sep. 1, 2011

Related U.S. Application Data

(60) Provisional application No. 61/296,610, filed on Jan. 20, 2010, provisional application No. 61/305,824, filed on Feb. 18, 2010, provisional application No. 61/314,883, filed on Mar. 17, 2010, provisional application No. 61/332,007, filed on May 6, 2010, provisional application No. 61/362,070, filed on Jul. 7, 2010, provisional application No. 61/368,898, filed on Jul. 29, 2010, provisional application No. 61/420,008, filed on Dec. 6, 2010.

(51) Int. Cl.
*A61B 17/22* (2006.01)
*A61F 11/00* (2006.01)

(52) U.S. Cl.
USPC ............................................ 606/159; 606/108

(58) Field of Classification Search
USPC ................. 606/108, 159, 169, 170, 190, 191; 604/22
See application file for complete search history.

(56) References Cited

U.S. PATENT DOCUMENTS

| 4,046,149 | A |   | 9/1977  | Komiya |
|-----------|---|---|---------|--------|
| 4,471,777 | A |   | 9/1984  | McCorkle, Jr. |
| 4,582,056 | A |   | 4/1986  | McCorkle, Jr. |
| 5,441,510 | A | * | 8/1995  | Simpson et al. ............... 606/159 |
| 5,651,781 | A |   | 7/1997  | Grace |
| 5,680,860 | A |   | 10/1997 | Imran |
| 5,693,030 | A | * | 12/1997 | Lee et al. ....................... 604/117 |
| 5,785,715 | A |   | 7/1998  | Schatz |
| 5,938,645 | A | * | 8/1999  | Gordon .......................... 604/264 |
| 5,947,983 | A | * | 9/1999  | Solar et al. ..................... 606/144 |
| 5,954,720 | A |   | 9/1999  | Wilson et al. |
| 6,060,695 | A |   | 5/2000  | Harle et al. |
| 6,183,469 | B1 |  | 2/2001  | Thapliyal et al. |
| 6,379,351 | B1 |  | 4/2002  | Thapliyal et al. |
| 6,419,674 | B1 |  | 7/2002  | Bowser et al. |

(Continued)

OTHER PUBLICATIONS

International Search Report based on PCT/US2011/021935 mailed Mar. 23, 2011.

(Continued)

*Primary Examiner* — Tuan V Nguyen
(74) *Attorney, Agent, or Firm* — Greenberg Traurig, LLP; Chin H. Pham; Roman Fayerberg

(57) ABSTRACT

Systems and methods for extraction of implanted articles are disclosed. According to aspects illustrated herein, there is provided a system for extraction of an implanted article that includes an elongated member, guide member disposed at a distal section of the elongated member and having a pathway in substantially parallel relationship to the elongated member, through which pathway an implanted article can be accommodated, and a cutting mechanism, situated between the distal section of the elongated member and the guide member, for severing a fibrous adhesion about the implanted article to allow the implanted article to be extracted.

14 Claims, 14 Drawing Sheets

(56) References Cited

U.S. PATENT DOCUMENTS

| | | |
|---|---|---|
| 7,344,546 B2 | 3/2008 | Wulfman et al. |
| 2008/0154296 A1 | 6/2008 | Taylor et al. |
| 2008/0275403 A1 | 11/2008 | Maaskamp et al. |
| 2009/0264831 A1 | 10/2009 | Thompson et al. |

OTHER PUBLICATIONS

International Search Report based on PCT/US2011/021895 mailed Mar. 25, 2011.

Office Action issued for U.S. Appl. No. 13/010,680 dated Dec. 28, 2012.

* cited by examiner

SYSTEMS AND METHODS FOR REMOVAL OF INTRAVASCULAR LEADS

RELATED APPLICATIONS

This application claims priority to and benefits of U.S. Provisional Application No. 61/296,610, filed Jan. 20, 2010, U.S. Provisional Application No. 61/305,824, filed Feb. 18, 2010, U.S. Provisional Application No. 61/314,883, filed Mar. 17, 2010, U.S. Provisional Application No. 61/332,007, filed May 6, 2010, U.S. Provisional Application No. 61/362,070, filed Jul. 7, 2010, U.S. Provisional Application No. 61/368,898, filed Jul. 29, 2010, and U.S. Provisional Application No. 61/420,008, filed Dec. 6, 2010. The entirety of all of these applications are hereby incorporated herein by reference for the teachings therein.

TECHNICAL FIELD

The presently disclosed embodiments relate to systems and methods for removal of implanted articles, and more particularly to systems and methods for removal of intravascular leads from blood vessels.

BACKGROUND

Implantable pacemakers and automatic implantable defibrillators contain intravascular leads that are typically inserted into a blood vessel of a patient, for instance, the internal jugular or subclavian vein. Such a lead can be advanced into the heart, where the distal section of the lead can be attached to the endocardial surface. Over time, however, the lead may fracture and become non-functional, so that a new lead may need to be inserted to replace the existing lead. The inoperative lead may also need to be removed from the vascular system, overtime, as it may get infected and may increase likelihood of blood clot formation. Removal of an inoperative lead, however, is oftentimes difficult because such a lead may have become ingrown within the vascular system, where fibrous adhesions may have formed between the lead and blood vessels.

Inoperative lead, in general, may sometimes be removed by simply pulling the free end of the lead to separate the lead from fibrous adhesions. However, this may lead to the creation of emboli in the blood stream by dislodging the fibrous adhesions in whole or in part, and may result in severe complication or even death of the patient. Several systems have been proposed for removal of inoperative leads. For example, U.S. Pat. No. 4,582,056 to McCorkle, Jr. et al. discloses a system that places a locking stylet inside the lead, enabling the physician to place traction on the lead. Sheaths of increasing diameter may then be advanced over the lead and rotated to disrupt the adhesions and allow lead removal. Because most leads have a substantially soft body, when an extraction sheath is advanced, the lead will tend to buckle and bunch up in front of the distal cutting end of the sheath. The buckling lead can increase the potential for the extraction sheath to veer out of axial alignment with the vein, and cut through the wall of the vein during advancement. This potential of the lead to bunch up and veer out of axial alignment can be increased in more recent extraction systems, because the more recent systems also include laser or radiofrequency cutting energy in addition to an extraction sheath.

Accordingly, there is a need for improved systems and methods for extraction of implanted articles, that can easily extract intravascular leads without some of the issues noted.

SUMMARY OF THE INVENTION

According to aspects illustrated herein, there is provided a system for extraction of an implanted article that includes an elongated member and a guide member disposed at a distal section of the elongated member. The guide member, in an embodiment, includes a pathway, in substantially parallel relationship to the elongated member, and through which an implanted article can be accommodated. The system can further include a cutting mechanism, situated between the distal section of the elongated member and the guide member, for severing a fibrous adhesion about the implanted article to allow the implanted article to be extracted.

According to aspects illustrated herein, there is further provided a system for extraction of an implanted article that includes a guide member. The system also includes a pathway defined by the guide member and configured to accommodate an implanted article therethrough. The system further includes a cutting mechanism positioned adjacent to the pathway, so as to enable the cutting mechanism to sever a fibrous adhesion about the implanted article on a luminal side of the implanted article.

According to aspects illustrated herein, there is provided further a method for extraction of an implanted article. To extract an implanted article, a proximal end of the implanted article may be accommodate in a pathway defined by a guide member. Next, a cutting mechanism may be positioned adjacent to the guide member, such that the cutting mechanism is oriented to sever an adhesion about the implanted article on a luminal side of the implanted article. The guide member in combination with the cutting mechanism may then be positioned distally of a site of the adhesion. Subsequently, the adhesion may be severed by the cutting mechanism and separated from the implanted article.

DESCRIPTION OF SPECIFIC EMBODIMENTS

Figure 1A:
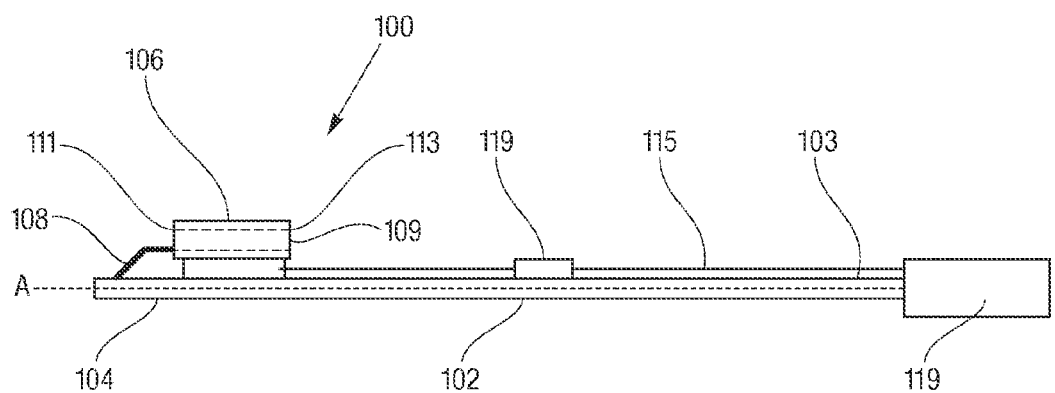
FIG. 1A is a schematic view of an extraction system of the present disclosure.

An extraction system 100 for removal of an implanted article, such a pacemaker lead, is shown generally in FIG. 1A. The extraction system 100 includes, in one embodiment, an elongated member 102 having a proximal section 103, a distal section 104, and a longitudinal axis A extending the length of the elongated member 102. The elongated member 102 may be designed to navigate along a guide wire, a guide catheter, or both to a site of fibrous adhesion about an implanted article. To that end, the member 102 may be sufficiently rigid axially along its length, while remaining sufficiently flexible radially from side to side. To provide the elongated member with such characteristic, in an embodiment, the elongated member 102 may be made from a plastic or metallic material or a combination thereof. If desired, the elongated member 102 may be made from an inelastic material to provide the elongated member with additional radial rigidity. In an embodiment, the elongated member 102 may also be made from a biocompatible material. The elongated member may also include material that can minimize or reduce friction, as the elongated member 102 travels to a site of fibrous adhesion about the implanted article. To further minimize friction, alternatively or additionally, the elongated member may be coated with a hydrophilic coating, such as, for example, polyvinylpyrrolidone, polyurethane, poly(acrylic acid), poly(methacrylic acid), poly(dimeth)acrylamide, PTFE, poly(acrylamide), polyvinybutyrol, poly(hydroxyethylmethacrylate) or combinations thereof. The elongated member 102 may also be coated with an anti-thrombogenic coating, such as heparin (or its derivatives), urokinase, or PPack (dextrophenylalanine proline arginine chloromethylketone) to prevent thrombosis or any other adverse reaction due to the introduction of the elongated member 102 into the body of a patient. Other components of the extraction system 100, as will be described below, may also be coated with a hydrophilic coating, a anti-thrombogenic coating, or both.

Figure 1B:
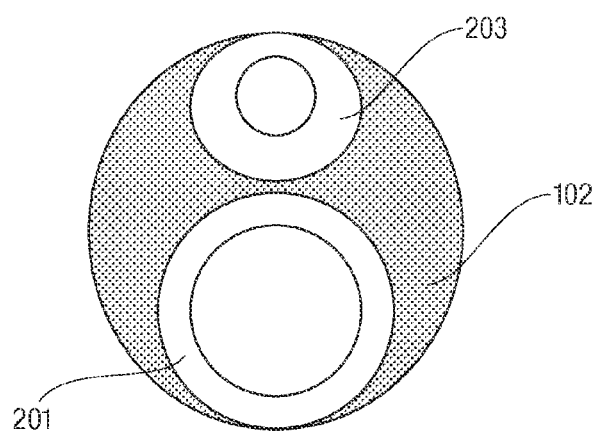
FIG. 1B is a cross sectional view of an elongated member of an extraction system of the present disclosure.

In an embodiment, the elongated member 102 may include one or more inner lumens 201, 203 for passing materials or instrumentation therethrough, as illustrated in FIG. 1B. The inner lumens 201, 203 may include a coating layer, as described above, to minimize or reduce friction as the materials or instruments are passed through the lumens. At least one lumen of the elongated member 102 may be dimensioned to accept a guide wire, a guide catheter, or both to enable the elongated member 102 to navigate to a site of fibrous adhesion about the implanted article.

The extraction system 100 can further include a cutting mechanism 108 disposed at the distal section 104 of the elongated article 102 to sever a fibrous adhesion around the implanted article. In an embodiment, the cutting mechanism 108 can be disposed between the elongated member 102 and a guide member 106, so that the cutting mechanism 108 can sever the fibrous adhesion on the luminal side of the implanted article, i.e., the side of the implanted article opposite to the point of tethering of the implanted article to tissue, for example, a blood vessel. Severing fibrous adhesions on the luminal side may decrease likelihood that the cutting mechanism 108 may come in contact and cause damage to tissue to which the implanted article is tethered, such as a blood vessel. It should be noted that the term "between" as used throughout this disclosure refers to the relative position of the cutting mechanism with respect to the elongated member and the guide member and is not intended to designate the specific location of the cutting mechanism, for instance, that the cutting mechanism is directly underneath the guide member, with respect to the elongated member. Rather, the term "between" is used to generally describe a spatial position of the elongated member, the cutting mechanism and the guide member with respect to one another.

To the extent necessary, the cutting mechanism 108 may be designed to be of any size, length, height, thickness, or geometric shape. In an embodiment, the height and/or shape of the cutting mechanism 108, as well as the relative position of the cutting mechanism 108 and the guide member 106, may be selected to enable the cutting mechanism 108 to sever a fibrous adhesion in a manner sufficiently close to the implanted article. In that way, the fibrous adhesion can be easily separated from the implanted article, such as, by advancing the guide member 106. Suitable cutting mechanisms include, but are not limited to, a blade, electrocautery, electrical wire, cutting electrode, any other mechanism capable of severing fibrous tissue. In an embodiment, the extraction system 100 may include a blade for mechanical severing of the fibrous adhesion and means, such as electrical wire, for heating the blade, the guide member or both in order to enhance severing and separating the fibrous adhesion from the implanted article.

Figure 2A:
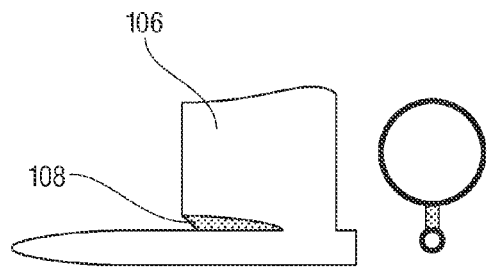
FIGS. 2A-2E illustrate various embodiments of an extraction system of the present disclosure with a stationary cutting mechanism.
Figure 2B:
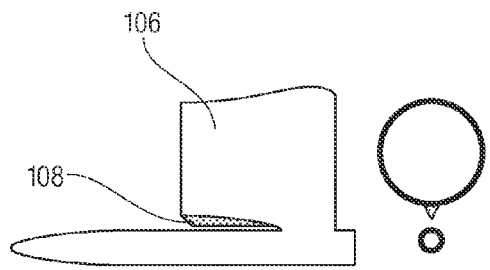
Figure 2C:
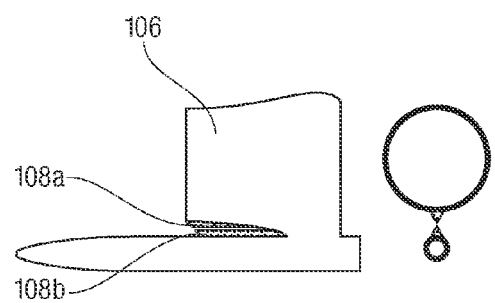
Figure 2D:
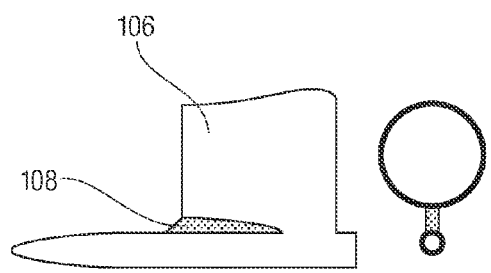
Figure 2E:
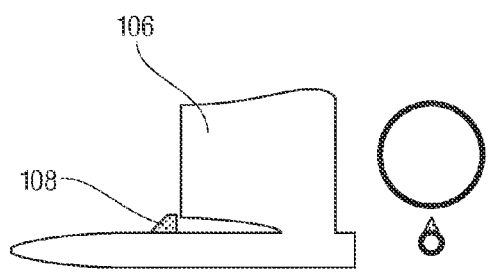

In some embodiments, the cutting mechanism 108 may be stationary with respect to the elongated member 102. For example, FIGS. 2A-2E illustrate various embodiments of the extraction system 100 with a stationary cutting mechanism 108. In some embodiments, the cutting mechanism 108 may be shielded by the guide member 106. In particular, the cutting mechanism 108 may be positioned substantially entirely underneath the guide member 106, as shown in FIGS. 2A, 2B and 2C. In other embodiments, a portion of the cutting mechanism 108 may be positioned distally of the guide member 106, as shown in FIG. 2D. In yet other embodiments, the cutting mechanism 108 may be positioned substantially entirely distal to the guide member 106 and 2E. In some embodiments, as illustrated in FIG. 2C, the extraction system 100 may include multiple cutting mechanisms 108a and 108b.

Figure 3A:
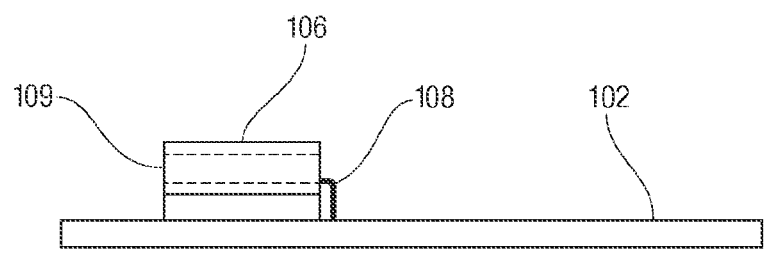
FIGS. 3A-3B illustrate an embodiment of an extraction system of the present disclosure with a translating cutting mechanism.
Figure 3B:
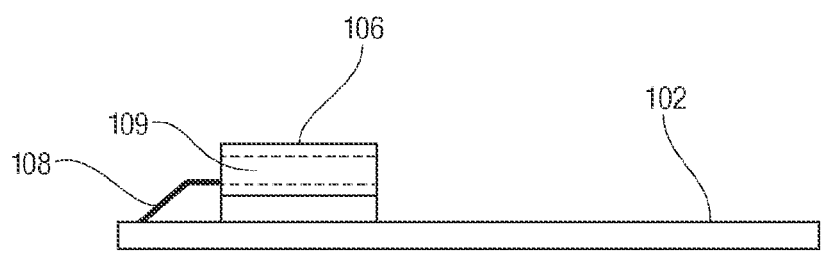

In other embodiments, such as shown in FIGS. 3A-3B, the cutting mechanism 108 may translate with respect to the elongated member 102 from a first retracted position, as shown in FIG. 3A, to a second advanced position, as shown in FIG. 3B. In an embodiment, the cutting mechanism 108 may translate substantially along the longitudinal axis A of the elongated member 102. In one embodiment, the translation of the cutting mechanism 108 may be between about 2 mm and about 10 mm. In another embodiment, the translation of the cutting mechanism may be about 5 mm.

Referring back to FIG. 1A, in some embodiments, the cutting mechanism 108 may include a control member 115 attached to a distal end of the cutting mechanism 108, so that the cutting mechanism 108 can be translated, with respect to the elongated member 102, from a first retracted position to a second advanced position. To advance and retract the cutting mechanism 108, an actuator 119 may be provided. The actuator 119 may be connected to a proximal end of the control member 115 in order to actuate the cutting mechanism 108. In an embodiment, as shown in FIG. 1A, the actuator may be positioned at the proximal section 103 of the elongated member 102. Of course, it should be understood that the actuator 119 may be positioned anywhere along the elongated member 102 or may not be attached to the elongated member 102.

Figure 9A:
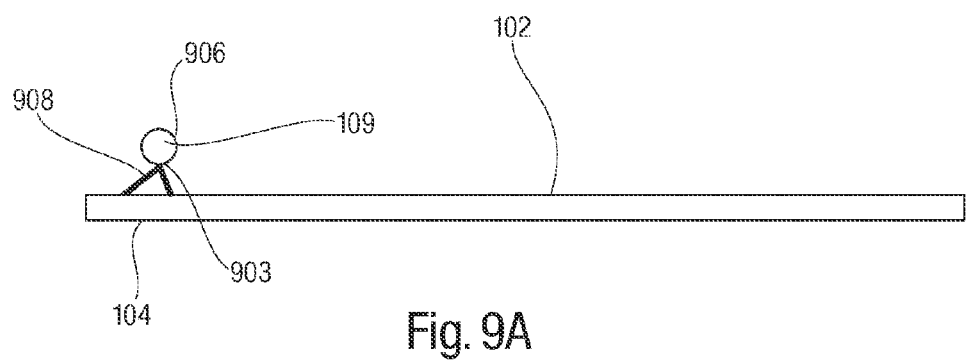
FIG. 9A is a schematic view of an embodiment of a guide member of an extraction system of the present disclosure.

The extraction system 100 can further include a guide member 106 positioned at the distal section 104 to the elongated member 102. The guide member 106 may include, in various embodiments, one or more tubes of various length or, for instance, any other design capable of accommodating the implanted article. For example, open or closed loops or rings, such as illustrated in FIG. 9A, can be used. In another embodiment, the guide member 106 may have a length sufficient to accommodate substantially the entire length of the implanted article. By providing the guide member 106 with such a length, the implanted article may remain within the guide member 106 following separation of the implanted article from the surrounding tissue to potentially prevent further contact between the implanted article and the surrounding tissue, and can aid in the ease of the removal of the implanted article from the body of the patient. It should be appreciated that while the extraction system 100 may be described and illustrated as having a single guide member 106, the extraction system 100 may include multiple guide members 106. Moreover, although the guide member 106 is described and illustrated herein as a separate element, it should be appreciated that in certain embodiments, one or more inner lumens of the elongated member 102 may serve as the guide member 106.

As illustrated in FIG. 1A, the guide member 106 can define a pathway 109 through which an implanted article can extend and be accommodated. In an embodiment, the pathway 109 may be substantially parallel to the longitudinal axis A of the elongated member 102. In another embodiment, the pathway 109 may be configured to position the implanted article received in the pathway 109 substantially parallel to longitudinal axis A of the elongated member 102.

The pathway 109, in an embodiment, can be configured to substantially secure the implanted article within the pathway 109. In this way, when a fibrous adhesion around the implanted article is severed, the implanted article can remain securely within the pathway 109. The pathway 109, in one embodiment, may be of any length, as long as the implanted article being accommodated in the pathway 109 can receive sufficient support. Moreover, the pathway 109 may be sized so that the pathway 109 forms a substantially snug fit over the implanted article, while still allowing the guide member 106 to move over and about the implanted article. In an embodiment, the pathway 109 may be provided with any design that may enable the pathway 109 to securely receive and accommodate an implanted article. Accordingly, the design of the pathway 109, may vary depending on the requirements of a particular procedure, that is, depending on the shape and size (i.e., diameter) of the implanted article to be extracted. It should be noted that the guide member 106 may be provided with a size and shape that compliment the size and shape of pathway 109. Alternatively, guide member 106 may be of a different size and shape in comparison to pathway 109.

The guide member 106, as shown in FIG. 1A, can also include a leading edge 111 and a trailing edge 113. In an embodiment, the leading edge 111 of the guide member 106 may be configured to separate the severed fibrous adhesion from the implanted article, so the implanted article can be freed from the adhesion for subsequent removal. The leading edge 111 of the guide member 106, by design, may be able to separate fibrous adhesion from the implanted article by virtue of its size, shape, surface character or combinations thereof. To that end, in an embodiment, the leading edge 111 of the guide member 106 may be sharpened and/or tapered to enhance separation of the fibrous adhesion from the implanted article. It should be appreciated that any design known in the art for providing a sharpened and/or tapered edge may be employed in connection with the leading edge 111 of the guide member 106. In an embodiment, the guide member 106, or its leading edge 111, may be heated to further enhance separation of the implanted article form the fibrous adhesion.

Figure 4:
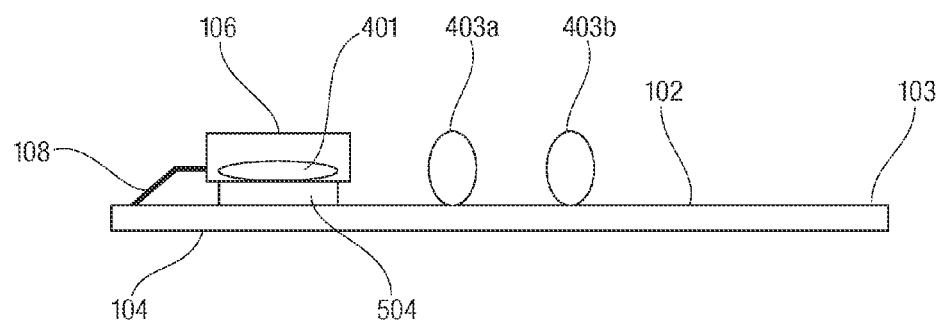
FIG. 4 illustrates an embodiment of an extraction system of the present disclosure having a gripping mechanism disposed within a guide member.

In embodiments where the cutting mechanism 108 may translate with respect to the elongated member 102, the guide member 106 may include, as illustrated in FIG. 4, a grasping mechanism 401 disposed within the pathway 109 of the guide member 106. The grasping mechanism 401 may be employed to secure the implanted article in place, as the cutting mechanism 108 severs a fibrous adhesion around the implanted article. Such securing of the implanted article can decrease the likelihood of the cutting mechanism 108 deviating from the fibrous adhesion and injuring a healthy tissue adjacent to the implanted article. The grasping mechanism 401, in one embodiment, may be a balloon, inflatable sleeve or cuff, or any adjustable mechanisms capable of securing the implanted article within the guide member 106. Additionally or alternatively, the extraction system 100 may include one or more loops 403a, 403b that may be employed to secure the implanted article in place. Loops 403a, 403b may have an inner diameter that can be releasably adjusted, when the implanted article extends there-through, to secure the implanted article in place.

Figure 5:
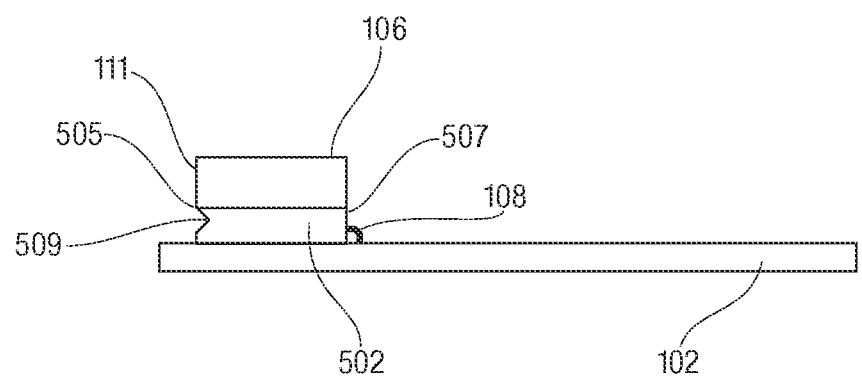
FIG. 5 is a schematic view of an embodiment of a guide member of an extraction system of the present disclosure.

Referring now to FIG. 5, there is illustrated another embodiment of the guide member 106. In the embodiment illustrated in FIG. 5, the guide member 106 includes an attachment section 502, which may allow the guide member 106 to be attached to the elongated member 102. The attachment section 502 may or may not be of a similar length and/or height as the guide member 106. In an embodiment, the attachment section 502 may be configured to house the cutting mechanism 108 and may be provided with sufficient spacing to allow the cutting mechanism 108 to translate between a first retracted position, in which the cutting mechanism 108 may be housed inside the attachment section 502 as shown in FIG. 5, and a second advanced position, in which the cutting mechanism 108 may be positioned substantially distally of the attachment section 502. The attachment section 502 may include a leading edge 505 and a trailing edge 507. In an embodiment, a notch 509 may be formed in the leading edge 505 of the attachment section 502. The presence of the notch 509 may allow a fiborus adhesion to be cradled or stabilized thereat as the fibrous adhesion is being severed.

Figure 6A:
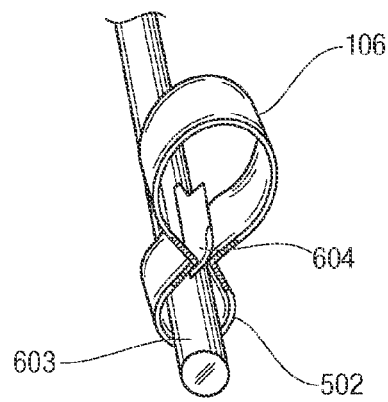
FIGS. 6A-6C illustrate an embodiment of the guide member of FIG. 5.
Figure 6B:
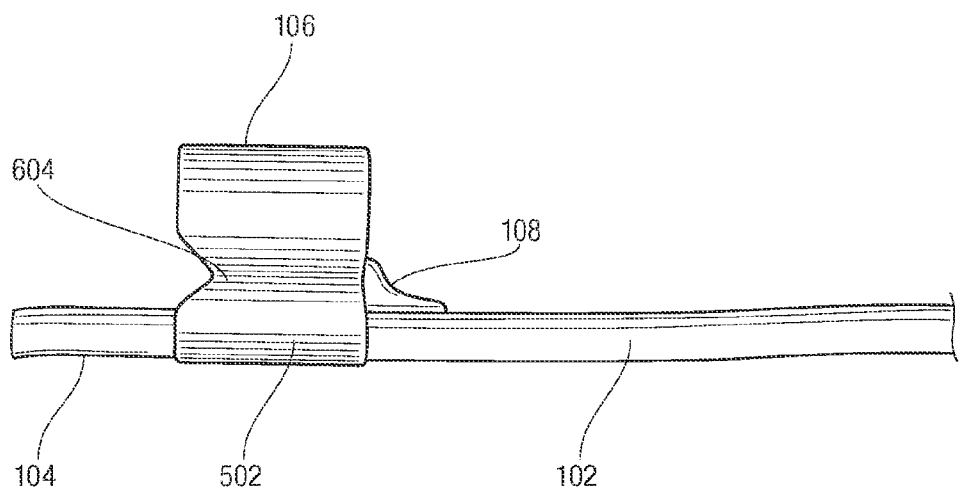
Figure 6C:
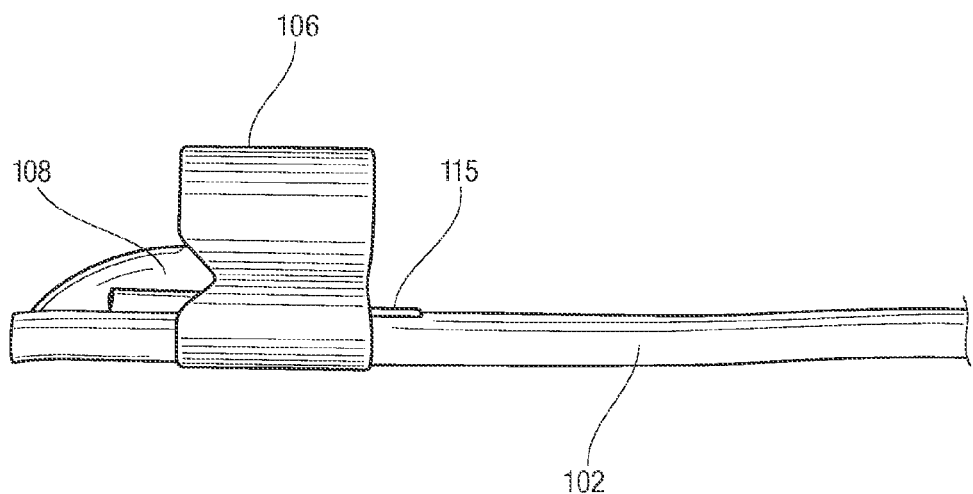
Figure 7A:
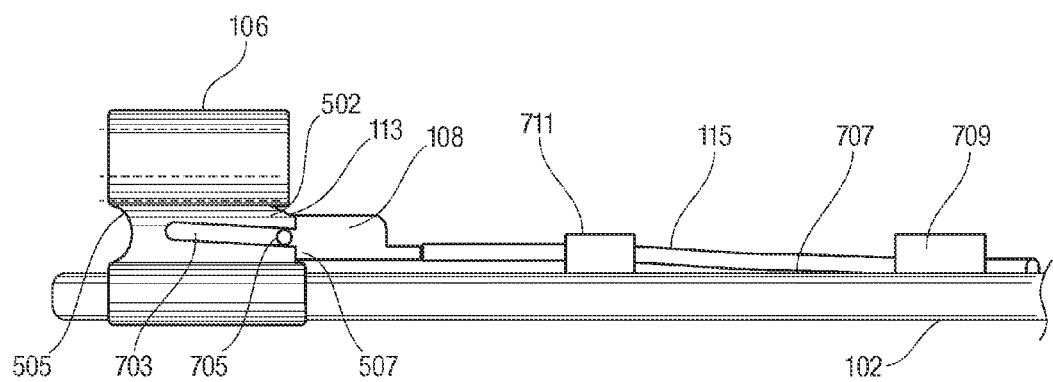
FIGS. 7A-7B illustrate another embodiment of the guide member of FIG. 5.
Figure 7B:
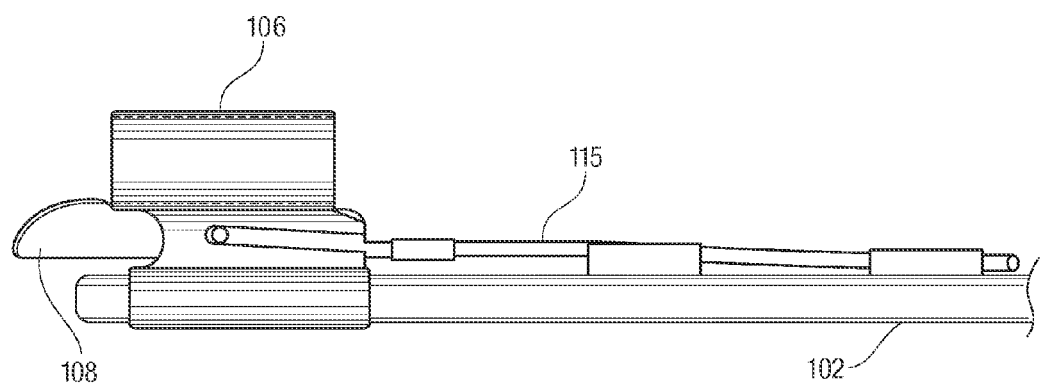

In a non-limiting example of the guide member 108, illustrated in FIGS. 6A-6D, the attachment section 502 may define a channel 604 designed to direct the movement of the cutting mechanism 108 along a defined path. In an embodiment, such defined path may be a substantially straight line along the longitudinal axis A of the elongated member 102. The channel 604 may be sized to ensure that in operation the cutting mechanism 108 does not deviate from a fibrous adhesion around the implanted article and cut a healthy tissue adjacent to the implanted article. To further restrain the movement of the cutting mechanism 108 along the defined path, in an embodiment, as illustrated in FIGS. 7A and 7B, the attachment section 502 may include guide slots 703 between the leading edge 505 and the trailing edge 507 of the attachment section 502. The guide slots 703, in one embodiment, may be configured to accept guide pins 705 disposed on each side of the cutting mechanism 108, such that the guide slots 703 form a track for the cutting mechanism 108 to translate between the first retracted position, as shown in FIG. 7A, and the second advanced position, as shown, in FIG. 7B. In an embodiment, the guide pins 705 and guide slots 703 may be configured so as to enable the cutting mechanism 108 to translate in a substantially straight line along the longitudinal axis A of the elongated member 102. In an embodiment, the guide slots 703 may be formed at an angle with respect to the longitudinal axis A of the elongated member 102, so that the cutting mechanism may cut progressively deeper into a fibrous adhesion as the cutting mechanism 108 moves from the first retracted position to the second advanced position.

Figure 8:
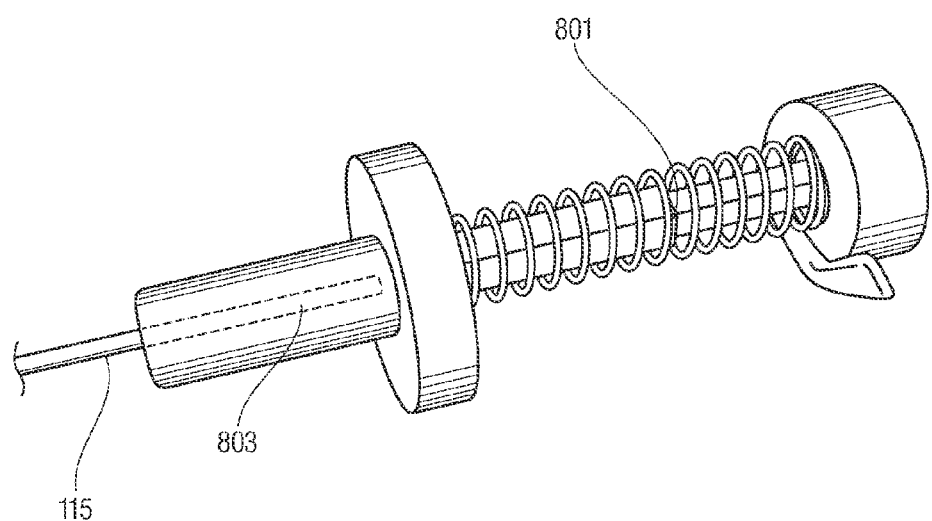
FIG. 8 illustrates an embodiment of an actuator suitable for use with embodiments of an extraction system of the present disclosure shown in FIGS. 6A-6D and 7A-7C.

As noted above in reference to FIG. 1A, the extraction system 100 may include the control member 115 and the actuator 119 for actuating the cutting mechanism 108. The control member 115 may be a wire, a rod or any other device capable of translating the cutting mechanism 108. Such a control member 115 may be passed through a cutting mechanism lumen 603 as shown in FIG. 6A, inside the elongated member 102, and may be attached to the cutting mechanism 108 for actuating the cutting mechanism 108 between the first retracted position, as shown in FIG. 6B, and the second advanced position, as shown in FIG. 6C. In another embodiment, illustrated in FIGS. 7A-7B, the control member 115 may extend along an outer surface 707 of the elongated member 102. In such embodiments, to stabilize the control member 115 in the longitudinal direction, one or more channels 709, 711 may be provided along the outer surface 707 of the elongated member 102 for passing the control member 115 therethrough. The control member 115 may be attached to the cutting mechanism 108 to actuate the cutting mechanism 108 between the first retracted position, as shown in FIG. 7A, and the second advanced position, as shown in FIG. 7B. In an embodiment, the control member 115 may be actuated using, for example, a spring loaded plunger 801, as shown in FIG. 8, attached to a distal section 803 of the control member 115.

In accordance with another embodiment of the present disclosure, as illustrated in FIG. 9A, a guide member 906 may be attached to the elongated member 102 via a cutting mechanism 908. Accordingly, the difference between this embodiment and the embodiment shown in FIG. 5 is that in this embodiment the cutting mechanism also serves as the attachment section of the embodiment of FIG. 5. The guide member 906, as illustrated in FIG. 9A, defines a pathway 909 for accommodating an implanted article, as described above in relation to the guide member 106. In such an embodiment, the guide member 906 may be disposed at an upper surface 903 of the cutting mechanism 908 substantially opposite a point at which the cutting mechanism 908 couples to the elongated member 102. In other words, the guide member 906 and the cutting mechanism 908 may be positioned radially away from the distal potion 104 of the elongated member 102. As in previously-described embodiments, the guide member 906 may be placed around the implanted article, so that the cutting mechanism 908 can be allowed to maintain a substantially uniform distance from a fibrous adhesion around the implanted article. In an embodiment, the cutting mechanism 908 may have a triangular shape. However, it should be understood that the cutting mechanism 908, similarly to the cutting mechanism 108, may be of any shape, so long as it can breach a fibrous adhesion. In various embodiments, the cutting mechanism 908 and the guide member 906 combination, as shown in FIG. 9, may be stationary or translatable with respect to the elongated member 102.

Figure 9B:
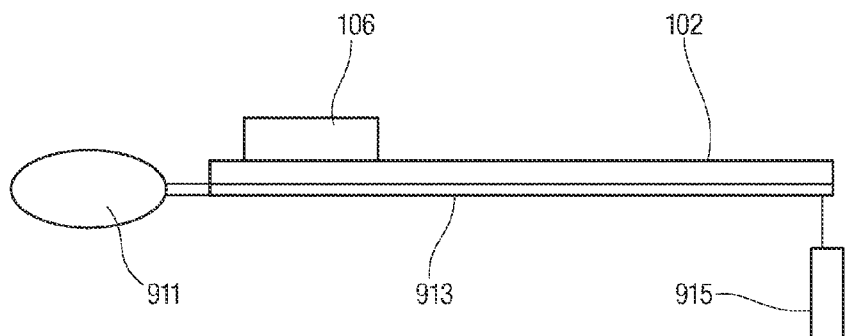
FIG. 9B is a schematic view of another embodiment of an extraction system of the present disclosure.

In another embodiment, as illustrated in FIG. 9B, the extraction system 100 of the present disclosure may include an inflatable member 911. The presence of inflatable member 911 may further aid in positioning the cutting mechanism 108 on the luminal side of the implanted article. In an embodiment, the inflatable member 109 may be positioned in a substantially opposing relationship to the guide member 108. The inflatable member 911 may have any design, such as a balloon, a ring, or a cuff. To operate the inflatable member 911, the extraction system 100 may further include an inflation tube 913 in fluid communication to the inflatable member 911 at one end, and a pump 915 at an opposite end. The inflation tube 933 may be disposed on the inside or outside the elongated member 102.

Figure 9C:
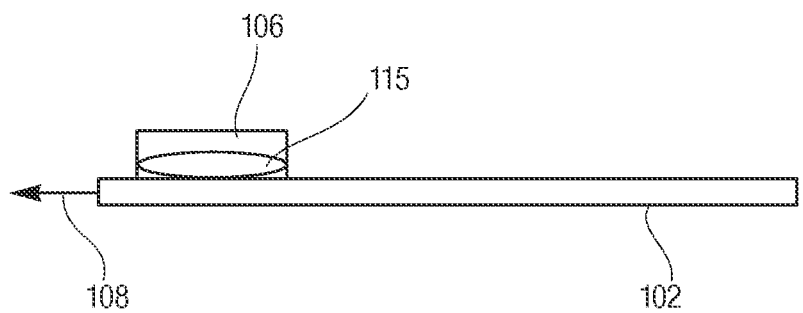
FIG. 9C is a schematic view of yet another embodiment of an extraction system of the present disclosure.

Yet another embodiment of the extraction system 100 of the present disclosure is illustrated in FIG. 9C. In such an embodiment, the cutting instrument 108 may be delivered through an inner lumen of the elongated member 102 and extend from the elongated member 102 to sever a fibrous adhesion. To be able to pass the cutting mechanism 109 through an inner lumen of the elongated member, the cutting mechanism 108 may be selected from a dissection probe, a dissection needle or a similar dissection mechanism.

Figure 10:
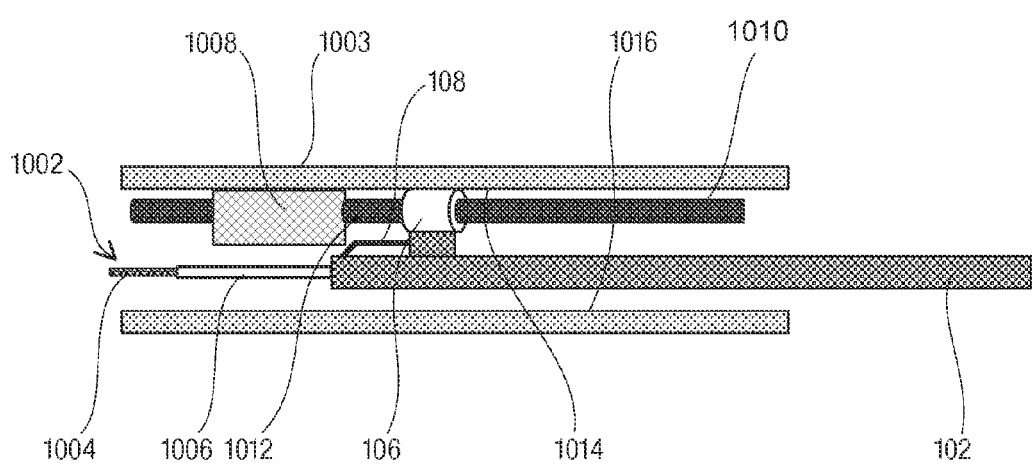
FIG. 10 shows an embodiment an extraction system of the present disclosure in operation.

In operation, the extraction system 100 may be utilized to sever a fibrous adhesion about an implanted article, such as a pacemaker lead, so as to enable ease of removal of the implanted article. In an embodiment, as illustrated in FIG. 10, a fibrous adhesion 1008 may exist between an implanted article 1010 and a vessel wall 1003 of a vessel 1002, such as a wall of a blood vessel, adhering the implanted article 1010 to the vessel wall 1003. To gain access to the vessel 1002 to perform the extraction protocol, in an embodiment, a needle may first be used to provide an opening in the vessel 1002 through which a guide wire 1004, a guide catheter 1006 or both may be inserted to define a pathway for the elongated member 108 to navigate the site of fibrous adhesion 1008. The guide wire 1004, guide catheter 1006 or both may be designed to provide sufficient strength and rigidity to support the elongated member.

The elongated member 102 may then be directed over the guide wire, the guide catheter or both to the site of fibrous adhesion 1008. In an embodiment, before, or shortly after, the elongated member 102 enters the vessel 1002, the implanted article 1010 may be inserted into the guide member 106, 906 to help orient the guide member and to position it on the on the luminal side 1014 of the implanted article 1010, so that the fibrous adhesion 1008 about the implanted article 1010 may be severed on the luminal side 1012 of the implanted article 1010, i.e. the side of the fibrous adhesion 1008 opposite the point of tethering of the implanted article 1010 to the vessel wall 1014. In such an embodiment, the guide member 106 may also support the implanted article 1010 during the subsequent removal of the implanted article 1010. The guide member 106, 906 may also aid in maintaining a desired distance between the cutting mechanism 108, 908 and the implanted article 1010, as the cutting mechanism 108, 908 severs the fibrous adhesion 1008 surrounding the implanted article 1010. By doing so, the cutting mechanism 108 can make a substantially uniform cut in the fibrous adhesion 1008 surrounding the implanted article 1010, which may subsequently aid in separating the implanted article 1010 from the fibrous adhesion 1008.

In the embodiments in which the extraction system 100 includes the inflatable member 911, as illustrated in FIG. 9B, upon insertion of the extraction system 100 into the vessel 1002, the inflatable member 911 can be inflated to permit subsequent engagement with the implanted article, for example, along a wall 1016 of the vessel 1002 opposite the wall 1014, to which the implanted article 1010 is tethered by the fibrous adhesion 1008. Such a design may further aid in maintaining the cutting mechanism 108 on the luminal side 1012 of the implanted article 1010.

During the delivery of the elongated member 102 to the site of fibrous adhesion 1008, the cutting mechanism 108, 908 in one embodiment, can stay in the retracted position. Upon encountering the fibrous adhesion 1008, the cutting mechanism 108, 908 may be actuated to the advanced position, as shown in FIG. 10, to sever the fibrous adhesion 1008 surrounding the implanted article 1010 along the luminal side 1012 of the implanted article 1010. If necessary, the cutting mechanism 108, 908 may be repeatedly moved back and forth between the advanced position and the retracted position until the fibrous adhesion 1008 is severed.

In embodiments where the guide member 106, 906 includes the grasping mechanism 401, the grasping mechanism 401 may be activated to grasp the implanted article 1010 and hold the implanted article in place before actuating the cutting mechanism 108, 908. Once the implanted article 1010 is secured, the cutting mechanism 108 may be used to dissect the fibrous adhesion 1008. Following dissection of the fibrous adhesion 1008, the grasping mechanism 401 may be deactivate to release the implanted article 1010 so that the elongated member 102 can be advanced in the distal direction, if desired.

Once the fibrous adhesion 1008 has been severed along the luminal side, the fibrous adhesion 1008 may be separated from the implanted article 1010, thus substantially eliminating a connective bond between the implanted article 1010 and the blood vessel 1002. In one embodiment, the guide member 106, 906 may be advanced distally across the fibrous adhesion 10008 to substantially separate the fibrous adhesion 1008 from the implanted article 1010. In another embodiment, the fibrous adhesion 1008 may be separated from the implanted article 1010 by simply manipulating the implanted article 1010, such as by pulling on the implanted article 1010, rotating the implanted article 1010, or both. In yet another embodiment, the fibrous adhesion 1008 may separate from the implanted article 1010 by virtue of severing the fibrous adhesion 1008, without any further actions.

The elongated member 102 may then be advanced distally to a site of another adhesion between the implanted article 1010 and the vessel 1002 to sever that adhesion and to substantially eliminate another connective bond between the implanted article 1010 and the vessel 1002. This process may be repeated until all connective bonds between the implanted article 1010 and the vessel 1002 have been eliminated. It should be noted that some adhesions may be severed or spliced open by the guide member 106, 906 itself, based on its design, without the help of the cutting mechanism, as the elongated member 102 is being advanced along the vessel. Once all connective bonds between the implanted article 1010 and the vessel 1002 have been eliminated, the implanted article 1010 can be removed from the body of the patient.

Figure 11:
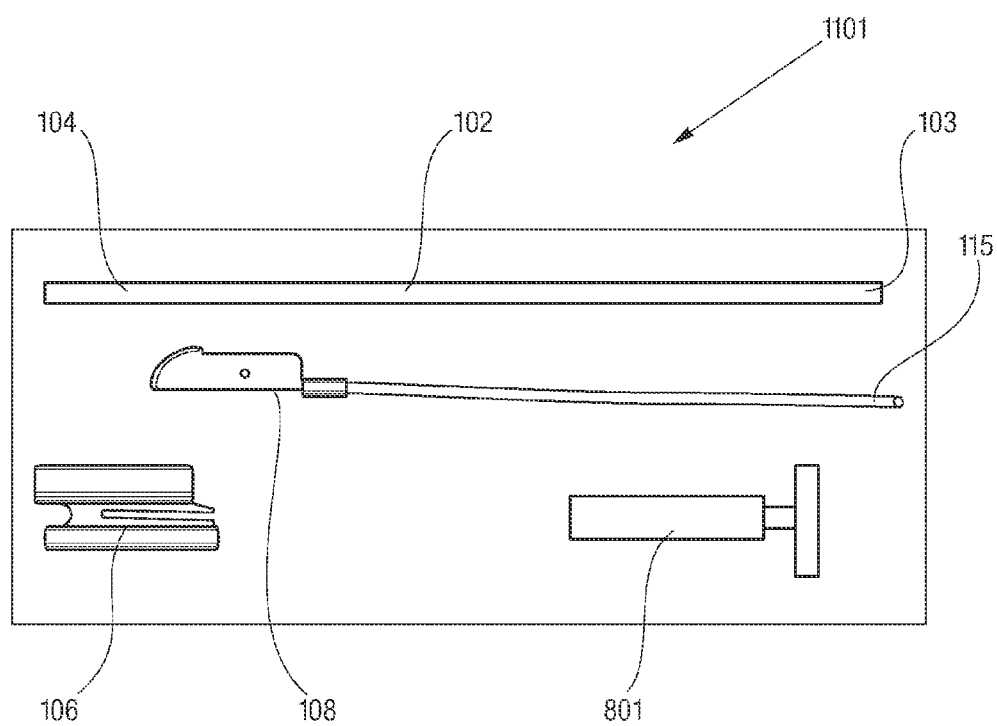
FIG. 11 is a top view of an embodiment of a kit for extraction of the present disclosure.

Referring to FIG. 11, in another aspect, a kit 1101 for extraction of an implanted article is provided. The kit 1101 may include an elongated member 102 with a proximal section 103, a distal section 104, and a longitudinal axis therebetween. The elongated member 102 may include one or more inner lumens configured to accept a guide wire, a guide catheter, or both, so that the elongated member can be navigated to a site of fibrous adhesion. The kit 1101 may also include a guide member 106 to be attached to the elongated member 102 at the distal section 104 of the elongated member 102. The guide member 106 may define a pathway 109 for receiving an implanted article. In an embodiment, when the guide member 108 is attached to the elongated member, the pathway 109 may extend in a substantially parallel relationship to the elongated member. A cutting mechanism 108 to be attached between the elongated member 102 and the guide member 106 may also be provided by the kit 1101. In an embodiment, the guide member 106 and the cutting mechanism 108 may be provided as a single unit. In another embodiment, as illustrated in FIG. 11, the guide member 106 and the cutting mechanism 108 may be provided separately. The cutting mechanism 108 may include a control member 115 attached to its distal end, so that, when the cutting mechanism 108 is attached to the elongated member 102, the cutting mechanism 108 can be translated with respect to the elongated member 102 from a first retracted position to a second advanced position. In an embodiment, the cutting mechanism 108 may translate substantially along the longitudinal axis of the elongated member. The control member 115 may be attachable to the elongated member 102 on the inside of the elongated member 102, such as by passing the control member through an inner lumen of the elongated member 102, or on the outside of the elongated member 102, such as by passing the control member through one or more channels (not shown) disposed on the surface of the elongated member. Moreover, the kit 1101 may also include an actuator 801, such as a spring loaded plunger, to be attached to the proximal end of the control member 115 for actuating the control member 115 and the cutting mechanism 108. It should of course be understood that the kit 1101 may include the guide member 906 and the cutting mechanism 908 in addition to or instead of the guide member 106 and the cutting mechanism 108.

Figure 12:
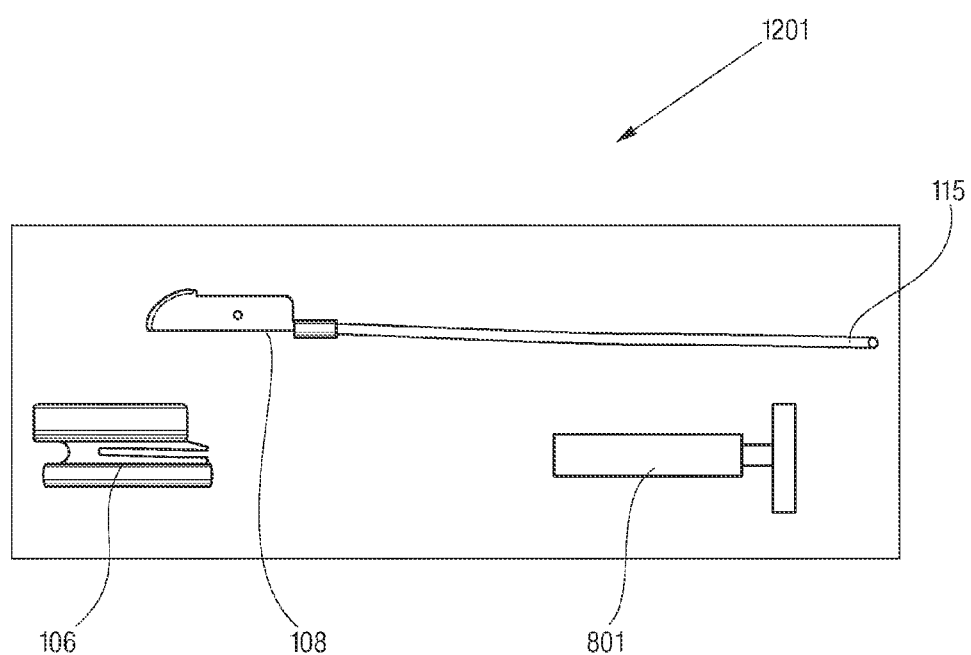
FIG. 12 is a top view of another embodiment of a kit for extraction of the present disclosure.

According to further aspects illustrated herein, there may be provided a kit 1201 for extraction of an implanted article. In the kit 1201, there may be provided a guide member 106 defining a pathway 109 configured to accommodate an implanted article therethrough. The kit 1201 may also include a cutting mechanism 108 configured to be positioned in relation to the pathway 109 so as to enable the cutting mechanism 108 to sever a fibrous adhesion about the implanted article on a luminal side of the implanted article. In an embodiment, the guide member 106 and the cutting mechanism 108 may be configured for attachment to an elongated member. In an embodiment, the guide member 106 and the cutting mechanism 108 may be provided as a single unit. In another embodiment, as illustrated in FIG. 12, the guide member 106 and the cutting mechanism 108 may be provided separately. The cutting mechanism 108 may include a control member 115 attached to its distal end for translating the cutting mechanism 108 from a first retracted position to a second advanced position. The kit 1201 may also include an actuator 119 for actuating the control member 115 and the cutting mechanism 108. It should be noted again that, similarly to the kit 1011, the kit 1201 may include the guide member 906 and the cutting mechanism 908 in addition to or instead of the guide member 106 and the cutting mechanism 108.

The extraction of the implanted article may, in an embodiment, may be monitored using an endoscopic technique or any other medical imaging technique. In an embodiment, an endoscope may be advanced through the elongated member to be placed in proximity to a fibrous adhesion being severed. Other suitable imaging techniques for monitoring extraction of the implanted article include, but are not limited to, x-ray, fluoroscopy, magnetic resonance imaging (MRI), ultrasound imaging, Fourier transform infrared spectroscopy, ultraviolet or visible spectroscopy.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. An extraction system comprising:

an elongated member;

a guide member disposed at a distal section of the elongated member and having a pathway in a substantially parallel relationship to the elongated member, the pathway having a central axis and being configured to receive an implanted article therethrough, the implanted article being attached to a tissue surface by a fibrous adhesion, the guide member being attached to the elongated member by an attachment section having guide slots extending between a leading edge and a trailing edge of the attachment section, the guide slots being configured to receive guide pins disposed on each side of the cutting mechanism; and a cutting mechanism situated entirely between the elongated member and the central axis of the guide member, the cutting mechanism having a cutting edge being positioned along a portion of the cutting mechanism and spaced apart from the central axis for severing the fibrous adhesion about the implanted article in a linear manner on a side of the implanted article away from the tissue surface to allow the implanted article to be extracted.

2. The system of claim 1, wherein the guide member is configured to maintain the cutting mechanism at a substantially uniform distance from the implanted article received in the pathway of the guide member.

3. The system of claim 1, wherein the guide member comprises a loop attached to an upper surface of the cutting mechanism.

4. The system of claim 1, wherein the cutting mechanism extends from the attachment section into the guide member.

5. The system of claim 1, wherein the pathway of the guide member is configured to receive an elongated tubular implanted article.

6. The system of claim 1 wherein the cutting mechanism translates substantially along a longitudinal axis of the elongated member from a first retracted position to the second advanced position.

7. The system of claim 1 wherein the guide member is configured to maintain the cutting mechanism on a luminal side of the implanted article.

8. An extraction system comprising:

an elongated member;

a guide member disposed at a distal section of the elongated member and having a pathway in a substantially parallel relationship to the elongated member, the pathway having a central axis and being configured to receive an implanted article therethrough, the implanted article being attached to a tissue surface by a fibrous adhesion, the guide member being attached to the elongated member by an attachment section having guide slots configured to receive guide pins disposed on each side of the cutting mechanism; and a cutting mechanism situated entirely between the elongated member and the central axis of the guide member, the cutting mechanism having a cutting edge being positioned along a portion of the cutting mechanism and spaced apart from the central axis for severing the fibrous adhesion about the implanted article on a side of the implanted article away from the tissue surface to allow the implanted article to be extracted.

9. The system of claim 8 wherein the guide member is configured to maintain the cutting mechanism at a substantially uniform distance from the implanted article received in the pathway of the guide member.

10. The system of claim 8 wherein the guide member comprises a loop attached to an upper surface of the cutting mechanism.

11. The system of claim 8 wherein the cutting mechanism extends from the attachment section into the guide member.

12. The system of claim 8 wherein the pathway of the guide member is configured to receive an elongated tubular implanted article.

13. The system of claim 8 wherein the cutting mechanism translates substantially along a longitudinal axis of the elongated member from a first retracted position to the second advanced position.

14. The system of claim 8 wherein the guide member is configured to maintain the cutting mechanism on a luminal side of the implanted article.

* * * * *